United States Patent [19]
Di Stefano et al.

[11] 3,932,135
[45] Jan. 13, 1976

[54] METHOD AND APPARATUS FOR THE DETERMINATION OF THE OXYGEN CONTENT OF METALLIC BATHS

[75] Inventors: Vittorio Di Stefano, Rome; Rinaldo Grimaldi, Genoa; Paolo Marini, Rome, all of Italy

[73] Assignee: Centro Sperimentale Metallurgico S.p.A., Rome, Italy

[22] Filed: Nov. 7, 1974

[21] Appl. No.: 521,850

[52] U.S. Cl. .................................. 23/253 R; 75/60
[51] Int. Cl.² ........................................ G01N 33/20
[58] Field of Search ............ 23/230 R, 253 R; 75/60

[56] References Cited
UNITED STATES PATENTS

| | | | |
|---|---|---|---|
| 3,188,180 | 6/1965 | Höller | 23/253 R X |
| 3,279,888 | 10/1966 | Höller | 23/253 R X |
| 3,661,559 | 5/1972 | Horvath et al. | 75/60 X |

*Primary Examiner*—Robert M. Reese
*Attorney, Agent, or Firm*—Young & Thompson

[57] ABSTRACT

An immersible probe for determining the oxygen content of a steel bath, having a disposable tip that contains aluminum, calcium, magnesium, titanium, zirconium or a rare earth metal that reacts exothermically with the bath oxygen to cause a temperature rise whose magnitude is proportional to bath oxygen content. In preferred embodiments, the probe tip captures a predetermined volume of the molten metal in a chamber having a closure of the metal of the bath which accordingly melts and exposes the chamber when the probe tip has penetrated beneath the slag. Plural chambers, one with oxidizable metal and one without, may be provided for precise comparison.

6 Claims, 3 Drawing Figures

METHOD AND APPARATUS FOR THE DETERMINATION OF THE OXYGEN CONTENT OF METALLIC BATHS

The present invention relates to an immersible probe for the determination of the oxygen content of metallic baths.

More particularly, the invention relates to an immersible probe for determining, in a simple, rapid and precise manner, the oxygen content of metallic baths as a function of the heat of reaction of the oxygen in a predetermined volume of the bath, with a substance that forms stable oxides.

As is known, during a number of metallurgical processes, and in particular in steelmaking, the problem arises of measuring one or more times the composition of the bath, particularly its oxygen content. In the case of steelmaking, for example, the carbon and oxygen contents are of particular interest owing to their great sensitivity to the variations of the operating parameters of the process as well as to their influence on the quality and properties of the product.

In steelmaking, a known method for measuring the oxygen content is to remove a sample from the bath, solidify it, and then analyze it in the laboratory by means of known methods. Although this method achieves high levels of precision, it is no longer of much use in steelmaking, especially in the case of oxygen steelmaking, as it takes too long to be acceptable.

Another known method consists in measuring the difference between the temperatures of the liquidus of a sample as cast and of a sample killed with aluminum. This method is faster than the first-mentioned method, but is less reliable both as to precision and as to sensitivity.

Still another method consists in the measurement of the electromotive force of a galvanic cell made up, on the one hand, of a reference electrode with constant oxygen activity as well as a solid electrolyte with transport of oxygen ions, and, on the other hand, of the steel bath which constitutes the electrode of unknown oxygen activity. This emf is a function of the oxygen activity in the bath and of temperature. A computer corrects the signal of the galvanic cell as to oxygen activity with respect to temperature and records the corrected result. This method is rapid but it has certain disadvantages, such as the high cost of the probe which must of necessity be of the expendable type, that is, utilizable only once. Also, this method is plagued by poor precision both at high and at low values of oxygen concentration, and by the need for frequent checks and calibration of the data transmission and display system.

Accordingly, it is an object of the present invention to provide apparatus for the determination of the oxygen content of metallic baths, which will overcome the above drawbacks and be rapid, economical, precise, sensitive, and low in cost.

Briefly, the objects of the present invention are achieved, by providing apparatus characterized by the measurement of temperature variation caused in part of the bath by the heat evolved by the reaction of a substance which forms a stable oxide with the oxygen in a predetermined volume of the bath.

More particularly, in the metallic bath whose oxygen content is to be measured, a probe having a disposable tip is inserted, having in the probe tip a device for the measurement of temperature and containing a predetermined quantity of a substance that forms a stable oxide. The substance is preferably a metal selected from the group consisting of aluminum, calcium, magnesium, titanium, zirconium, and a rare earth metal. By "rare earth metal" is meant lanthanum, cerium and other metals of atomic number 57–71 used for deoxidizing steel, yttrium, misch metal, etc.

Both the temperature measuring device and the oxide-forming substance are temporarily shielded by a consumable material such as a metal that melts in the bath, preferably the very metal of the bath, so as to allow the temperature-measuring device to reach thermal stability before the oxide-forming substance begins to react. The shield also permits the metal to react only when the end of the probe which carries the device is immersed in the metal bath and not in the slag.

When the metal bath and probe tip and temperature-measuring device are all at thermal equilibrium, the shield will be consumed or melted and the bath will come into contact with the oxide-forming substance in the immersed end of the probe, which in turn will react with the oxygen in the bath according to the equation $$x\, Me + y\, O_2 = Me_xO_{2y} - \Delta H$$

$\Delta H$, which is the exothermic heat of reaction, causes a temperature rise which is directly proportional to the quantity of oxygen which has reacted and to the mass of steel which contained that oxygen and inversely proportional to the thermal capacity of the system.

From this temperature rise, the oxygen concentration of the bath can be easily derived, as will be shown hereinafter.

An advantage of the present invention is that for determining the concentration of oxygen in a metallic bath, it is not necessary to know the temperature of the bath or the mass of steel containing the oxygen which has reacted. As regards the temperature of the bath, in fact, the quantity of heat which is evolved by the reaction of one mol of oxygen with the metal is constant, within 1 per cent, between 1300° and 1800°C., as is also the thermal capacity of the system. Accordingly, the temperature rise caused in the system by the said reaction of 1 mol of oxygen with the metal is also constant. As to the mass of steel involved in the reaction, the formula for temperature rise is as follows:

$$\Delta T = Q\, Me_xO_{2y}/Mcp = C_{02}\, M\, H\, /\, Mcp = C_{02}\, H\, /cp,$$

from which:

$$C_{02} = \Delta T cp\, /\, H$$

the thermal capacity of the measuring device, relative to that of the steel, is considered to be negligible in this instance, as in fact it is in reality.

In the above equations, the terms have the following meaning:

$\Delta T$ is the recorder change in temperature;
$QMe_xO_{2y}$ is the heat evolved by the reaction of formation of the oxide;
$cp$ is the specific heat of the steel;
$M$ is the mass of steel involved in the reaction;
$C_{02}$ is the oxygen content of the bath in grams/liter;
$H$ is the enthalpy of formation of the oxide $Me_xO_{2y}$.

It will be noted that the mass of steel involved in the reaction is not a factor in the final formula for the determination of the oxygen concentration.

Although it is not necessary to know the temperature of the steel bath in order to determine its oxygen content, as was pointed out above, nevertheless the measurement of this parameter is important for the correct operation of the steelmaking process. Thus, the temperature-measuring means of the present invention can also be used to measure the temperature of the bath at the same time as its oxygen content.

The procedure by which the present invention is practiced can comprise the following steps:

1. Measurement of the bath temperature;
2. Bringing into contact with the bath a quantity of a substance that reacts exothermically with oxygen dissolved in the bath to form a stable oxide, the quantity of this substance being in excess of that stoichiometrically required.
3. Measuring the variation in temperature caused locally in the bath by the reaction between the oxide-forming substance and the dissolved oxygen. From the value of this temperature variation it is possible, by use of the formula $$C_{o_2} = \Delta T \, cp \, / \, H$$

or by the use of suitable standard curves, to derive readily the oxygen content of the metallic bath.

The oxide-forming material is preferably present in excess of that necessary to react with the oxygen presumably contained in at least one cubic decimeter of metallic bath. In other words, under the operating conditions it is in stoichiometric excess.

The apparatus for practicing the present invention comprises a probe at least the tip of which is expendable, the tip comprising a hollow body containing the temperature-sensing element of a thermometric system, together with a substance that reacts exothermically with oxygen dissolved in the bath to form a stable oxide. The walls of the hollow body are formed, at least in part, by a consumable shield.

Other objects, features and advantages of the present invention will become apparent from a consideration of the following disclosure, taken in connection with the accompanying drawing, in which.

Figure 1:
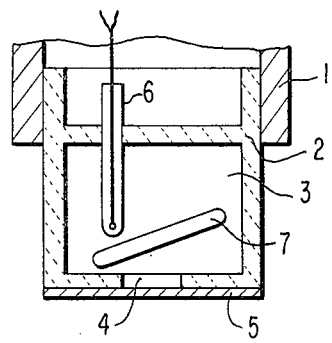
FIG. 1 is a cross-sectional view of the tip of a consumable probe according to the present invention, in a first embodiment thereof.

Referring now to the drawing in greater detail, and first to FIG. 1 thereof, there is shown a probe having a body 1 in the form of a hollow tube and a hollow body 2 of refractory material in the end thereof. Body 2 has an internal cavity 3 which communicates with the exterior through a hole 4 closed by a consumable shield 5, preferably of the same metal as the bath whose oxygen content is to be determined. In cavity 3 is disposed the thermosensitive element 6 of a thermometric device which is otherwise not shown but which is conventional. Element 6 may for example be a thermocouple.

A metallic capsule 7 contains the substance that reacts exothermically with the oxygen dissolved in the bath to form a stable oxide.

When the probe is immersed in the metallic bath, the consumable shield 5 allows the tip of the probe to penetrate the slag layer floating on the bath without the slag entering the cavity 3. Shield 5 and the walls of capsule 7 are of a thickness such as to permit the probe to reach the chosen measurement position, and to allow the thermometric system and the refractory body 2 to reach thermal equilibrium with the bath, before the molten metal of the bath melts shield 5 and comes into contact with the oxide-forming substance contained in capsule 7.

When this contact occurs, an exothermic reaction takes place which locally raises the temperature of the bath, the variation of bath temperature obtained in this way being directly correlated with oxygen content of the bath on the basis of the equation given above.

The reactive substance in capsule 7 is in stoichiometric excess relative to the oxygen in the molten metal in cavity 3, and so there will remain some unreacted substance when the exotherm ceases and the detected temperature stops rising.

Figure 2:
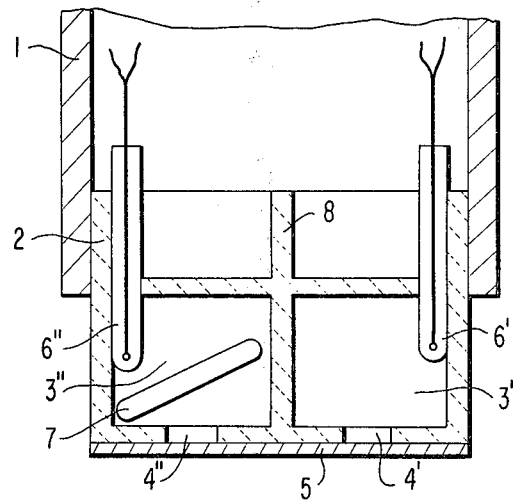
FIG. 2 is a view similar to FIG. 1 but showing a modified form of the probe tip.

FIG. 2 shows a second embodiment of probe tip according to the present invention. In this embodiment, differential measurements are carried out, the hollow body 2 having an internal vertical diaphragm 8 which is also of refractory material and which divides the internal cavity of body 2 into two separate compartments 3' and 3''. Compartment 3' contains the sensing element 6' of a thermometric device which is otherwise not shown but is conventional, for the measurement of the temperature of the metallic bath; while compartment 3'' contains the sensing element 6'' of a second thermometric device and the metallic capsule 7 containing the oxide-forming substance. Both compartments are provided with openings 4' and 4'', which are closed by a common consumable metal shield 5. The accuracy of measurement of the temperature rise due to the exotherm is thus improved by the side-by-side standardization provided by the embodiment of FIG. 2.

Figure 3:
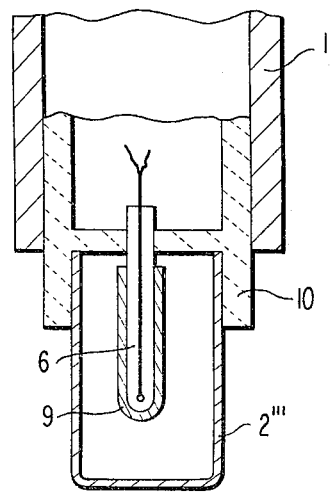
FIG. 3 is a view similar to FIGS. 1 and 2 but showing still another embodiment thereof.

FIG. 3 shows a third embodiment in which the walls of the hollow body 2''' are entirely metallic and also perform the function of the shield 5 of the embodiments of FIGS. 1 and 2. A connector 10 joins this cup-shaped hollow body 2''' to the probe 1.

The oxide-forming material in the embodiment of FIG. 3, instead of being in a capsule 7, is now in the form of a sheath 9 enclosing the temperature-sensing element 6 of the thermometric device. Sheath 9 is contacted by and reacts with the oxygen in the molten metal when hollow body 2''' melts.

In all embodiments, temperature sensed by elements 6, or the temperature difference sensed by elements 6' and 6'', will be displayed and/or recorded in a conventional manner by conventional apparatus which need not be further described, in terms of temperature as such and/or the correlative oxygen content.

From a consideration of the foregoing disclosure, therefore, it will be evident that the initially recited objects of the present invention have been achieved.

Although the present invention has been described and illustrated in connection with preferred embodiments, it is to be understood that modifications and variations may be resorted to without departing from the spirit of the invention, as those skilled in this art will readily understand. Such modifications and variations are considered to be within the purview and scope of the present invention as defined by the appended claims.

Having described our invention, we claim:

1. Apparatus for the determination of the quantity of oxygen dissolved in a metallic bath, comprising a probe having at its tip a hollow body, a thermometric device in said hollow body, a substance in said hollow body that reacts exothermically with oxygen dissolved in the bath to form a stable oxide, and a consumable shield comprising at least a portion of said hollow body to prevent contact between said substance and the metallic bath until after said thermometric device has reached thermal equilibrium with the bath.

2. Apparatus as claimed in claim 1, said hollow body being of refractory material having at least one opening therethrough that is closed by said shield.

3. Apparatus as claimed in claim 1, said hollow body being of refractory material having two chambers in one of which is disposed said thermometric device and said substance and in the other of which is disposed a second thermometric device for comparison, both said chambers being closed by a consumable shield.

4. Apparatus as claimed in claim 1, in which said substance is a member selected from the group consisting of calcium, magnesium, aluminum, titanium, zirconium and a rare earth metal.

5. Apparatus as claimed in claim 1, said consumable shield comprising a cup surrounding said substance.

6. Apparatus as claimed in claim 5, in which said substance is in the form of a sheath about said thermometric device.

* * * * *